United States Patent [19]
Clark et al.

[11] Patent Number: 5,698,545
[45] Date of Patent: Dec. 16, 1997

[54] ANGIOSTATIC STEROIDS AND METHODS AND COMPOSITIONS FOR CONTROLLING OCULAR HYPERTENSION

[75] Inventors: Abbot F. Clark, Arlington; Raymond E. Conrow, Fort Worth, both of Tex.

[73] Assignee: Alcon Laboratories, Inc., Fort Worth, Tex.

[21] Appl. No.: 643,387

[22] Filed: May 6, 1996

Related U.S. Application Data

[63] Continuation of Ser. No. 349,342, Dec. 2, 1994, abandoned, which is a continuation of Ser. No. 941,485, Sep. 8, 1992, Pat. No. 5,371,078, which is a continuation-in-part of Ser. No. 559,123, Jul. 27, 1990, abandoned, which is a continuation-in-part of Ser. No. 419,226, Oct. 10, 1989, abandoned, which is a continuation of Ser. No. 264,918, Oct. 31, 1988, Pat. No. 4,876,250.

[51] Int. Cl.$^6$ ............................................. A61K 31/57
[52] U.S. Cl. ........................................ 514/179; 514/182
[58] Field of Search ........................... 514/169, 172, 514/173, 174, 175, 176, 177, 178, 179, 180, 181, 182

[56] References Cited

U.S. PATENT DOCUMENTS

| | | | |
|---|---|---|---|
| 4,617,299 | 10/1986 | Knepper | 514/178 |
| 4,812,448 | 3/1989 | Knepper | 514/178 |
| 4,863,912 | 9/1989 | Southren et al. | 514/177 |
| 5,371,078 | 12/1994 | Clark et al. | 514/182 |

OTHER PUBLICATIONS

Crum, et al., *Science*, vol. 230, pp. 1375–1378 (Dec. 1985), "A New Class of Steroids Inhibits Angiogenesis in the Presence of Heparin or a Heparin Fragment".

Ingber, et al., *Endocrinology*, vol. 119, pp. 1768–1775 (1986), "A Possible Mechanism for Inhibition of Angiogenesis by Angiostatic Steroids" Induction of Capillary Basement Membrane Dissolution.

Southern, et al., *Investigative Ophthalmology and Visual Science*, vol. 28, pp. 901–903 (May 1987), "Intraocular Hypotensive Effect of a Topically Applied Cortisol Metabolite: 3-alpha-5, beta-tetrahydrocortisol".

Folkman, et al., *Ann. Surg.*, vol. 206(3):, pp. 374–382, (1987), "Angiostatic Steroids".

Rohen, Johanness W., *Ophthalmology*, vol. 90(7), pp. 758–764, (1983), "Why is Intraocular Pressure Elevated in Chronic Simple Glaucoma?".

Knepper, et al., *Pediatric Neuroscience*, vol. 12, pp. 240–251, (1985/86), "Glycosaminoglycans and Outflow Pathways of the Eye and Brain".

*Primary Examiner*—Kimberly J. Prior
*Attorney, Agent, or Firm*—Sally Yeager

[57] ABSTRACT

Angiostatic steroids for use in controlling ocular hypertension are disclosed. Pharmaceutical compositions of the angiostatic steroids and methods for their use in treating ocular hypertension, including controlling the ocular hypertension associated with primary open angle glaucoma, are disclosed. In addition, the combination of the compounds with glucocorticoids for the prevention of elevated IOP during the treatment of inflammation is disclosed.

3 Claims, No Drawings

ANGIOSTATIC STEROIDS AND METHODS AND COMPOSITIONS FOR CONTROLLING OCULAR HYPERTENSION

This application is a continuation of application Ser. No. 08/349,342, filed Dec. 2, 1994, now abandoned which is a continuation of Ser. No. 07/941,485 filed Sep. 8, 1992, now U.S. Pat. No. 5,371,078, which is a continuation-in-part of Ser. No. 07/559,123 filed Jul. 27, 1990 now abandoned which is a continuation-in-part of Ser. No. 07/419,226 filed Oct. 10, 1989 now abandoned, which is a continuation of Ser. No. 07/264,918 filed Oct. 31, 1988, now U.S. Pat. No. 4,876,250.

BACKGROUND OF THE INVENTION

1. Field of the Invention

This invention relates to angiostatic steroids and their use in methods and compositions for controlling ocular hypertension. Specifically, the invention is directed to new angiostatic steroids, pharmaceutical compositions comprising the angiostatic steroids, and methods of treatment comprising administering these compositions to treat ocular hypertension, including controlling ocular hypertension associated with primary open angle glaucoma. In addition, the compounds can be used in combination with glucocorticoids to control the ocular hypertension very commonly associated with the use of glucocorticoids in the treatment of ocular inflammation.

2. Description of Related Art

Steroids functioning to inhibit angiogenesis in the presence of heparin or specific heparin fragments are disclosed in Crum, et el., *A New Class of Steroids Inhibits Angiogenesis in the Presence of Heparin or a Heparin Fragment*, Science, Vol.230, pp.1375–1378 (Dec. 20, 1985). The authors refer to such steroids as "angiostatic" steroids. Included within the new class of steroids found to be angiostatic are the dihydro and tetrahydro metabolites of cortisol and cortexolone. In a follow-up study directed to testing a hypothesis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., *A Possible Mechanism for Inhibition of Angiogenesis by Angiostatic Steroids: Induction of Capillary Basement Membrane Dissolution*, Endocrinology 119, pp.1768–1775 1986).

A group of tetrahydro steroids useful in inhibiting angiogenesis is disclosed in International Patent Application No. PCT/U.S. Pat. No. 86/02189, Aristoff, et al., (The Upjohn Company). The compounds are disclosed for use in treating head trauma, spinal trauma, septic or traumatic shock, stroke and hemorrhage shock. In addition, the patent application discusses the utility of these compounds in embryo implantation and in the treatment of cancer, arthritis and arteriosclerosis. The compounds are not disclosed for ophthalmic use.

Tetrahydrocortisol (THF) has been disclosed for its use in lowering the intraocular pressure (IOP) of rabbits made hypertensive with dexamethasone alone, or with dexamethasone/5-beta-dihydrocortisol; see Southren, et al., *Intraocular Hypotensive Effect of a Topically Applied Cortisol Metabolite: 3-alpha, 5-beta-tetrahydrocortisol*, Investigative Ophthalmology and Visual Science, Vol.28 (May, 1987). The authors suggest THF may be useful as an antiglaucoma agent. In U.S. Pat. No. 4,863,912, issued to Southren et al. on Sep. 5, 1989, pharmaceutical compositions containing THF and a method for using these compositions to control intraocular pressure are disclosed. THF has been disclosed as an angiostatic steroid in Folkman, et al., *Angiostatic Steroids*, Ann. Surg., Vol.206, No.3 (1987) wherein it is suggested angiostatic steroids may have potential use for diseases dominated by abnormal neovascularization, including diabetic retinopathy, neovascular glaucoma and retrolental fibroplasia.

Many compounds classified as glucocorticoids, such as dexamethasone and prednisolone, are very effective in the treatment of inflammed tissues. When applied topically to the eye to treat ocular inflammation, these compounds cause elevations in intraocular pressure in certain patients. Patients who experience these elevations when treated with glucocorticoids are generally referred to as "steroid responders". The elevations are of particular concern in patients already suffering from elevated intraocular pressures, such as glaucoma patients. In addition, there is always a risk that the use of glucocorticoids in patients with normal intraocular pressures will cause pressure elevations resulting in damage to ocular tissue. Since glucocorticoid therapy is frequently long term (i.e., several days or more), there is potential for significant damage to ocular tissue as a result of prolonged elevations in intraocular pressure attributable to that therapy. Commonly assigned U.S. patent application Ser. No. 399, 351 discloses the use of the angiostatic steroid tetrahydrocortexolone, in combination with a glucocorticoid to prevent the intraocular pressure elevating effect of the glucocorticoid being used in the treatment of ophthalmic inflammation.

SUMMARY OF THE INVENTION

This invention is directed to steroids useful in inhibiting angiogenesis. The compounds can be used for treatment of, for example, head trauma, spinal trauma, septic or traumatic shock, stroke, hemorrhage shock, cancer, arthritis, and arteriosclerosis. In particular, the angiostatic steroids and compositions thereof are useful for controlling ocular hypertension. The compositions are particularly useful in the treatment of primary open angle glaucoma.

The invention encompasses methods for controlling ocular hypertension through the topical administration of the compositions disclosed herein.

Moreover, the invention includes the use of the angiostatic steroids in combination with a glucocorticoid being used to treat ocular inflammation. The angiostatic steroid makes it possible to employ the potent antiinflammatory glucocorticoids without producing significant elevations in intraocular pressure.

DETAILED DESCRIPTION OF PREFERRED EMBODIMENTS

The development of blood vessels for the purpose of sustaining viable tissue is known as angiogenesis. Agents which inhibit angiogenesis are known by a variety of terms such as angiostatic, angiolytic or angiotropic agents. For purposes of this specification, the term "angiostatic agent" means compounds which can be used to inhibit angiogenesis.

The angiostatic agents of the present invention are steroids or steroid metabolites. For purposes herein; the term "angiostatic steroids" means steroids and steroid metabolites which inhibit angiogenesis. The present invention is based on the finding that angiostatic steroids can be used for the control of ocular hypertension. In particular, the agents can be used for the treatment of primary open angle glaucoma.

The angiostatic steroids of the present invention have the following formula:

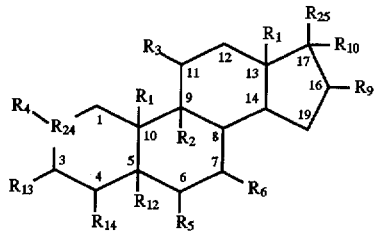
Structure [A]

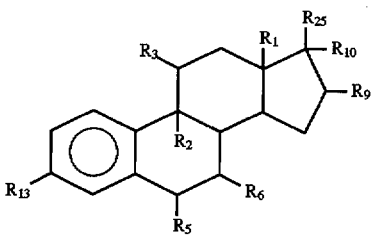
Structure [B]

wherein $R_1$ is H, β-$CH_3$ or β-$C_2H_5$; $R_2$ is F, $C_9$-$C_{11}$ double bond, $C_9$-$C_{11}$ epoxy, H or Cl; $R_3$ is H, $OR_{26}$, OC(=O)$R_{27}$, halogen, $C_9$-$C_{11}$ double bond, $C_9$-$C_{11}$ epoxy, =O, —OH, —O—alkyl ($C_1$-$C_{12}$), —OC(=O)alkyl($C_1$-$C_{12}$), —OC(=O)ARYL, —OC(=O)N(R)$_2$ or —OC(=O)$OR_7$, wherein ARYL is furyl, thienyl, pyrrolyl, or pyridyl and each of said moieties is optionally substituted with one or two ($C_1$-$C_4$) alkyl groups, or ARYL is —$(CH_2)_f$-phenyl wherein f is 0 to 2 and the phenyl ring is optionally substituted with 1 to 3 groups selected from chlorine, fluorine, bromine, alkyl ($C_1$-$C_3$), alkoxy($C_1$-$C_3$), thioalkoxy-($C_1$-$C_3$), $Cl_3C$—, $F_3C$—, —$NH_2$ and —$NHCOCH_3$ and R is hydrogen, alkyl ($C_1$-$C_4$), or phenyl and each R can be the same or different, and $R_7$ is ARYL as herein defined, or alkyl ($C_1$-$C_{12}$); $R_4$ is H, $CH_3$, Cl or F; $R_5$ is H, OH, F, Cl, Br, $CH_3$, phenyl, vinyl or allyl; $R_6$ is H or $CH_3$; $R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, O(C=O)$R_{27}$ or O(C=O)$CH_2C(=O)OR_{26}$ $R_{10}$ is —C≡CH, —CH=$CH_2$, halogen, CN, $N_3$, $OR_{26}$, OC(=O)$R_{27}$, H, OH, $CH_3$ or $R_{10}$ forms a second bond between positions C-16 and C-17; $R_{12}$ is H or forms a double bond with $R_1$ or $R_{14}$; $R_{13}$ is halogen, $OR_{26}$, OC(=O)$R_{27}$, $NH_2$, $NHR_{26}$, NHC(=O)$R_{27}$, N($R_{26}$)$_2$, NC(=O)$R_{27}$, $N_3$, H, —OH, =O, —O—P(=O)(OH)$_2$, or —O—C(=O)—(CH$_2$)$_t$COOH where t is an integer from 2 to 6; $R_{14}$ is H or forms a double bond with $R_{12}$; $R_{15}$ is H, =O or —OH; and $R_{23}$ with $R_{10}$ forms a cyclic phosphate; wherein $R_9$ and $R_{15}$ have the meaning defined above; or wherein $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond,—CON(R$_{18}$)—, —N(R$_{18}$)CO—, —O—, —S—, —S(O)—, or —S(O$_2$)—; $R_{18}$ is hydrogen or alkyl (C$_1$-C$_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5; Z is a bond or —O—; r is an integer of from 2 to 9; and Q is one of the following:

(1) —R$_{19}$—CH$_2$COOH wherein R$_{19}$ is —S—, —S(O)—, —S(O)$_2$—, —SO$_2$N(R$_{20}$)—, or N(R$_{20}$)SO$_2$—; and R$_{20}$ is hydrogen or lower alkyl-(C$_1$-C$_4$); with the proviso that the total number of carbon atoms in R$_{20}$ and (CH$_2$)$_r$ is not greater than 10; or (2) —CO—COOH; or (3) CON(R$_{21}$)CH(R$_{22}$)COOH wherein R$_{21}$ is H and R$_{22}$ is H, CH$_3$, —CH$_2$COOH, —CH$_2$CH$_2$COOH, —CH$_2$OH, —CH$_2$SH, —CH$_2$CH$_2$SCH$_3$, or —CH$_2$Ph—OH wherein Ph—OH is p-hydroxyphenyl; or R$_{21}$ is CH$_3$ and R$_{22}$ is H; or R$_{21}$ and R$_{22}$ taken together are —CH$_2$CH$_2$CH$_2$—; or —N(R$_{21}$)CH(R$_{22}$)COOH taken together is —NHCH$_2$CONHCH$_2$COOH; and pharmaceutically acceptable salts thereof; with the proviso that except for the compound wherein R$_1$ is β—CH$_3$, R$_2$ and R$_3$ taken together form a double bond between positions 9 and 11, R$_4$ and R$_6$ are hydrogen, R$_{12}$ and R$_{14}$ taken together form a double bond between positions 4 and 5, R$_5$ is α-F, R$_g$ is β—CH$_3$, R$_{10}$ is α—OH, R$_{13}$ and R$_{15}$ are =O and R$_{23}$ is —OP(O)—(OH)$_2$, R$_{13}$ is =O only when R$_{23}$ with R$_{10}$ forms the above described cyclic phosphate.

R$_{24}$=C, C$_1$-C$_2$ double bond, O;
R$_{25}$=C(R$_{15}$)CH$_2$—R$_{23}$, OH OR$_{26}$, OC(=O)R$_{27}$, R$_{26}$, COOH, C(=O)OR$_{26}$, CHOHCH$_2$OH, CHOHCH$_2$OR$_{26}$, CHOHCH$_2$OC(=O)R$_{27}$, CH$_2$CH$_2$OH, CH$_2$CH$_2$OR$_{26}$, CH$_2$CH$_2$OC(=O)R$_{27}$, CH$_2$CN, CH$_2$N$_3$, CH$_2$NH$_2$, CH$_2$NHR$_{26}$, CH$_2$N(R$_{26}$)$_2$, CH$_2$OH, CH$_2$OR$_{26}$, CH$_2$O(C=O)R$_{27}$, CH$_2$O(P=O) (OH)$_2$, CH$_2$O(P=O) (OR$_{26}$)$_2$, CH$_2$SH, CH$_2$S—R$_{26}$, CH$_2$SC(=O)R$_{27}$, CH$_2$NC(=O)R$_{27}$, C(=O)CHR$_{28}$OH, C(=O)CHR$_{28}$OR$_{26}$, C(=O)CHR$_{28}$OC(=O)R$_{27}$ or R$_{10}$ and R$_{25}$ taken together may be =C(R$_{28}$)$_2$, that is, an optionally alkyl substituted methylene group;

wherein R$_{26}$=C$_1$-C$_6$ (alkyl, branched alkyl, cycloalkyl, haloalkyl, aralkyl, aryl); R$_{27}$=R$_{26}$+OR$_{26}$; R$_{28}$=H, C1-C6 (alkyl, branched alkyl, cycloalkyl).

Excepted from the compounds of Structure [A] are the compounds wherein R$_1$ is β—CH$_3$ or β-C$_2$H$_5$; R$_2$ is H or Cl; R$_3$ is H, =O, —OH, —O—alkyl(C$_1$-C$_{12}$), —OC(=O)alkyl (C$_1$-C$_{12}$), —OC(=O)ARYL, —OC(=O)N(R)$_2$ or α—OC(=O)OR$_7$, wherein ARYL is furyl, thienyl, pyrrolyl, or pyridyl and each of said moieties is optionally substituted with one or two (C$_1$-C$_4$)alkyl groups, or ARYL is —(CH$_2$)$_f$-phenyl wherein f is 0 to 2 and the phenyl ring is optionally substituted with 1 to 3 groups selected from chlorine, fluorine, bromine, alkyl(C$_1$-C$_3$), alkoxy(C$_1$-C$_3$), thioalkoxy-(C$_1$-C$_3$), Cl$_3$C—, F$_3$C—, —NH$_2$ and —NHCOCH$_3$ and R is hydrogen, alkyl (C$_1$-C$_4$), or phenyl and each R can be the same or different, and R$_7$ is ARYL as herein defined, or alkyl (C$_1$-C$_{12}$); or wherein R$_2$ and R$_3$ taken together are oxygen (—O—) bridging positions C-9 and C-11; or wherein R$_2$ and R$_3$ taken together form a double bond between positions C-9 and C-11; or R$_2$ is α-F and R$_3$ is β-OH; or R$_2$ is α-Cl and R$_3$ is β-Cl; and R$_4$ is H, CH$_3$, Cl or F; R$_5$ is H, OH, F, Cl, Br, CH$_3$, phenyl, vinyl or allyl; R$_6$ is H or CH$_3$; R$_9$ is H, OH, CH$_3$, F or =CH$_2$; R$_{10}$ is H, OH, CH$_3$ or R$_{10}$ forms a second bond between positions C-16 and C-17; R$_{12}$ is —H or forms a double bond with R$_{14}$; R$_{13}$ is H, —OH, =O, —O—P(O)(OH)$_2$, or —O—C(=O)—(CH$_2$)$_t$COOH where t is an integer from 2 to 6; R$_{14}$ is H or forms a double bond with R$_{12}$; R$_{15}$ is =O or —OH; and R$_{23}$ with R$_{10}$ forms a cyclic phosphate; wherein R$_9$ and R$_{15}$ have the meaning defined above; or wherein R$_{23}$ is —OH, O—C(=O)—R$_{11}$, —OP(O)—(OH)$_2$, or —O—C(=O)—(CH$_2$)$_t$COOH wherein t is an integer from 2 to 6; and R$_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond,—CON(R$_{18}$)—, —N(R$_{18}$)CO—, —O—, —S—, —S(O)—, or —S(O$_2$)—; R$_{18}$ is hydrogen or alkyl (C$_1$–C$_4$); each of R$_{16}$ and R$_{17}$ is a lower alkyl group of from 1 to 4 carbon atoms optionally substituted with one hydroxyl or R$_{16}$ and R$_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5; Z is a bond or —O—; r is an integer of from 2 to 9; and Q is one of the following:

(1) —R$_{19}$—CH$_2$COOH wherein R$_{19}$ is —S—, —S(O)—, —S(O)$_2$—, —SO$_2$N(R$_{20}$)—, or N(R$_{20}$)SO$_2$—; and R$_{20}$ is hydrogen or lower alkyl-(C$_1$–C$_4$); with the proviso that the total number of carbon atoms in R$_{20}$ and (CH$_2$)$_r$ is not greater than 10; or (2) —CO—COOH; or (3) CON(R$_{21}$)CH(R$_{22}$)COOH wherein R$_{21}$ is H and R$_{22}$ is H, CH$_3$, —CH$_2$COOH, —CH$_2$CH$_2$COOH, —CH$_2$OH, —CH$_2$SH, —CH$_2$CH$_2$SCH$_3$, or —CH$_2$Ph—OH wherein Ph—OH is p-hydroxyphenyl; or R$_{21}$ is CH$_3$ and R$_{22}$ is H; or R$_{21}$ and R$_{22}$ taken together are —CH$_2$CH$_2$CH$_2$—; or —N(R$_{21}$)CH(R$_{22}$)COOH taken together is —NHCH$_2$CONHCH$_2$COOH; and pharmaceutically acceptable salts thereof; with the proviso that except for the compound wherein R$_1$ is β—CH$_3$, R$_2$ and R$_3$ taken together form a double bond between positions 9 and 11, R$_4$ and R$_6$ are hydrogen, R$_{12}$ and R$_{14}$ taken together form a double bond between positions 4 and 5, R$_5$ is α-F, R$_9$ is β-CH$_3$, R$_{10}$ is α-OH, R$_{13}$ and R$_{15}$ are =O and R$_{23}$ is —OP(O)—(OH)$_2$, R$_{13}$ is =O only when R$_{23}$ with R$_{10}$ forms the above described cyclic phosphate.

Also excepted from the compounds of Structure [A] are the compound 3,11β, 17α, 21-tetrahydroxy-5-pregnane-20-one (the 3-α, 5-β; 3-α, 5α; 3-β, 5-α; and 3-β, 5-β isomers of tetrahydrocortisol) wherein R$_{15}$ is =O, R$_{10}$ is α-OH, R$_1$ is β-CH$_3$, R$_3$ is β-OH, R$_2$ is H, R$_4$ is H, R$_{13}$ is α- or β-OH, R$_{14}$ is H, R$_{12}$ is α- or β-H, R$_5$ is H, R$_6$ is H, R$_9$ is H, R$_{24}$ is C, and R$_{23}$ is OH; and methyltestosterone, wherein R$_1$ is β-CH$_3$, R$_2$ is H, R$_3$ is H, R$_4$ is H, R$_5$ is H, R$_6$ is H, R$_9$ is H, R$_{10}$ is α-CH$_3$, R$_{12}$ and R$_{14}$ form a C$_4$–C$_5$ double bond, R$_{13}$ is =0, R$_{24}$ is C and R$_{25}$ is β-OH; dihydrotestosterone, wherein R$_1$ is β-CH$_3$, R$_2$R$_3$R$_4$R$_5$R$_6$R$_9$R$_{10}$R$_{14}$ are H, R$_{12}$ is α-H, R$_{13}$ is =0, R$_{24}$ is C, and R$_{25}$ is β-OH; dromostanolone propionate, wherein R$_1$ is β-CH$_3$, R$_2$R$_3$R$_4$R$_5$R$_6$R$_9$R$_{10}$R$_{14}$ are H, R$_{12}$ is α-H, R$_{13}$ is =0, R$_{24}$ is C and R$_{25}$ is β-OC(=O)CH$_2$CH$_3$; methandrostenelone, wherein R$_1$ is β—CH$_3$, R$_2$R$_3$R$_4$R$_5$R$_6$R$_9$ are H, R$_{10}$ is α-CH$_3$, R$_{12}$ and R$_{14}$ form a C$_4$C$_5$ double bond, R$_{13}$ is =0, R$_{24}$ is C$_1$C$_2$ double bond, and R$_{25}$ is β-OH; testosterone, wherein R$_1$ is β-CH$_3$, R$_2$R$_3$R$_4$R$_5$R$_6$R$_9$R$_{10}$ are H, R$_{12}$ and R$_{14}$ form a C$_4$C$_5$ double bond, R$_{13}$ is =0, R$_{24}$ is C, and R$_{25}$ is β-OH; norethandrolone, wherein R$_1$ is CH$_3$(C$_{13}$) and H(C$_{10}$), R$_2$R$_3$R$_4$R$_5$R$_6$ R$_9$ are H, R$_{10}$ is α-CH$_2$CH$_3$, R$_{12}$ and R$_{14}$ form a C$_4$–C$_5$ double bond, R$_{13}$ is =0, R$_{24}$ is C, and R$_{25}$ is β-OH; bolasterone, wherein R$_1$ is β—CH$_3$, R$_2$R$_3$R$_4$R$_5$R$_9$ are H, R$_6$ is α-CH$_3$, R$_{10}$ is α-CH$_3$, R$_{13}$ is =0, R$_{12}$ and R$_{14}$ form a C$_4$C$_5$ double bond, C$_{24}$ is C and R$_{25}$ is β-OH; and oxandrolone, wherein R$_1$ is β-CH$_3$, R$_2$R$_3$R$_5$R$_6$R$_9$R$_{14}$ are H, R$_{10}$ is αCH$_3$, R$_{12}$ is α-H, R$_{13}$ is =0, R$_{24}$ is O, and R$_{25}$ is β-OH.

Unless specified otherwise, all substituent groups attached to the cyclopentanophenanthrenemotety of Structures [A] and [B] may be in either the alpha or beta position. Additionally, the above structures include all pharmaceutically acceptable salts of the angiostatic steroids.

Preferred angiostatic steroids are:

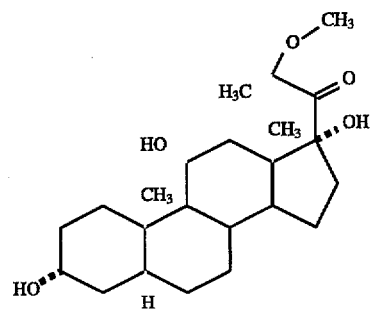

21-METHYL-5β-PREGNAN-3α, 11β, 17α, 21-TETROL-20-ONE 21-METHYL ETHER

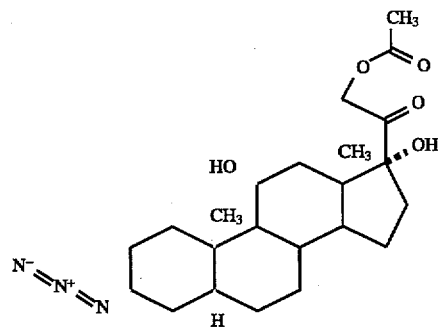

3β-AZIDO-21-ACETOXY-5β-PREGNAN-11β, 17α-DIOL-20-ONE

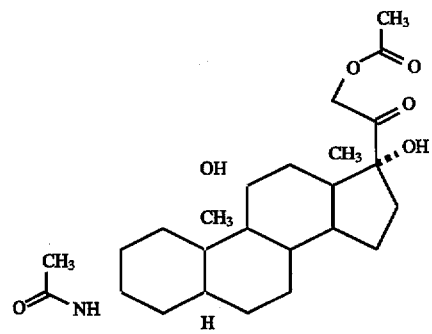

3β-ACETAMIDO-21-ACETOXY-5β-PREGNAN-11β, 17α-DIOL-20-ONE

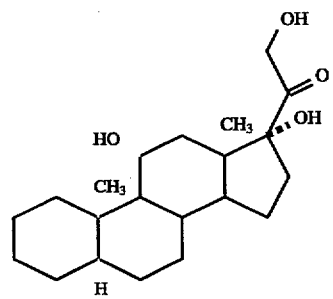

5β-PREGNAN-11β, 17α, 21-TRIOL-20-ONE

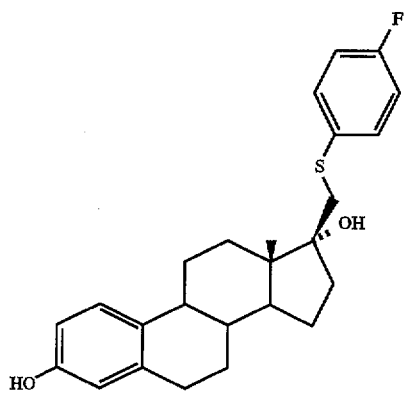
17-((4-FLUORO)THIOPHENOXY)METHYL-
1, 3, 5-ESTRATRIEN-3, 17-DIOL
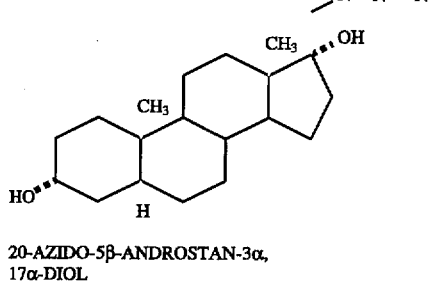
20-AZIDO-5β-ANDROSTAN-3α,
17α-DIOL
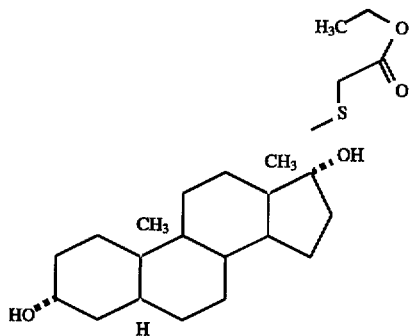
20-(CARBETHOXYMETHYL)THIO-5β-ANDROSTAN-
3α, 17α-DIOL
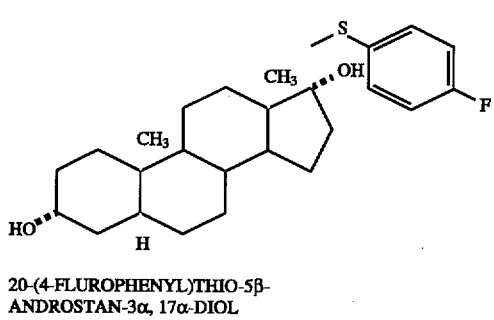
20-(4-FLUROPHENYL)THIO-5β-
ANDROSTAN-3α, 17α-DIOL
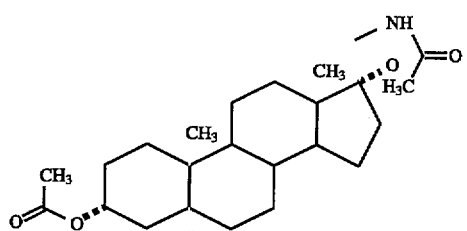
20-ACETAMIDO-3α-ACETOXY-5β-ANDROSTAN-
17α-OL
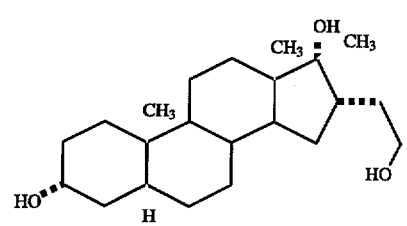
16α-(2-HYDROXYETHYL-17β-METHYL-
5β-ANDROSTAN-3α, 17α-DIOL
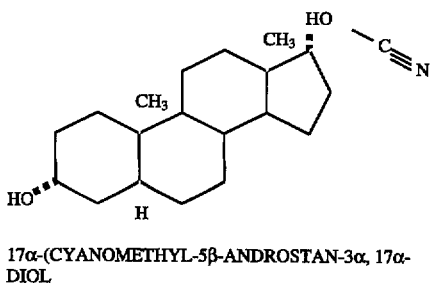
17α-(CYANOMETHYL-5β-ANDROSTAN-3α, 17α-DIOL
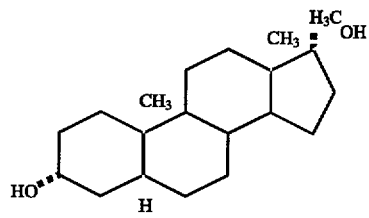
17α-METHYL-5β-ANDROSTAN-
3α, 17α- DIOL
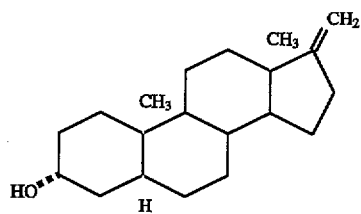
5β-ANDROST-17(20)-EN-3α-OL

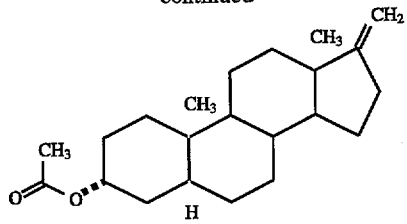

3α-ACETOXY-5α-ANDROST-17(20)-ENE

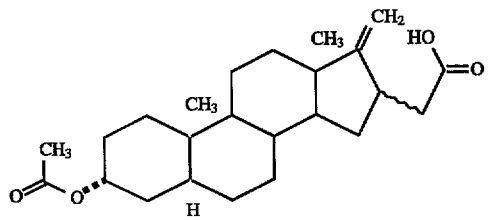

3α-ACETOXY-5α-ANDROST-17(20)-EN-16-ACETIC ACID

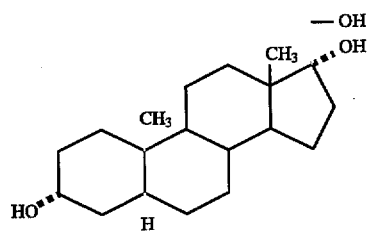

5β-ANDROSTAN-3α, 17α, 20-TRIOL

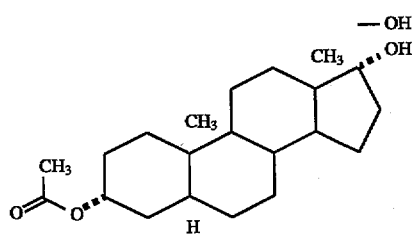

3α-ACETOXY-5β-ANDROSTAN-17α, 20-DIOL

MOST PREFERRED STEROID

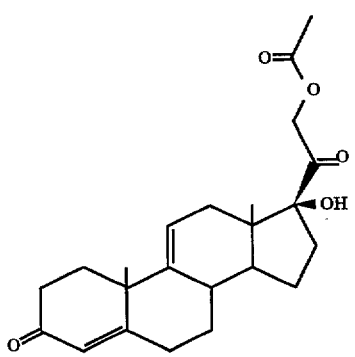

4,9(11)-PREGNADIEN-17α, 21-DIOL-3, 20-DIONE-21-ACETATE

The more preferred compounds are 21-methyl-5β-pregnan-3α, 11β, 17α,21-tetrol 20-one-21-methyl ether; 3β-azido-21-acetoxy-5β-pregnan-11β, 17α-diol-20-one; 3β-acetamido-21-acetoxy-5β-pregnan-11β, 17α-diol-20-one; and 5β-pregnan-11β, 17α, 21-triol-20-one. The most preferred compound is 4,9(11)-pregnadien-17α,21-diol-3, 20-dione-21-acetate.

Without intending to be bound by any theory, it is believed that the angiostatic steroids of the type described above act to control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering from POAG. However, it has been found that the amorphous extracellular material is generally composed of glycosaminoglycans (GAGs) and basement membrane material; see, *Ophthalmology*, Vol.90, No.7 (July 1983); *Mayo Clin. Proc*, Vol.61, pp.59–67 (Jan.1986); and *Pedtat. Neurosci.* Vol.12, pp.240–251 (1985–86). When these materials build up in the trabecular meshwork, the aqueous humor, normally present in the anterior chamber of the eye, cannot leave this chamber through its normal route (the trabecular meshwork) at its normal rate. Therefore, a normal volume of aqueous humor is produced by the ciliary processes of the eye and introduced into the anterior chamber, but its exit through the trabecular meshwork is abnormally slow. This results in a buildup of pressure in the eye, ocular hypertension, which can translate into pressure on the optic nerve. The ocular hypertension so generated can lead to blindness due to damage to the optic nerve.

Many methods for treating primary open angle glaucoma and ocular hypertension concentrate on blocking production of aqueous humor by the eye. However, aqueous humor is the fundamental source of nourishment for the tissues of the eye, particularly the cornea and lens which are not sustained by blood supply. Therefore, it is not desirable to deprive these tissues of the necessary irrigation and nutrition provided by the aqueous humor. It is desirable to strive for normal exit of the aqueous humor by maintaining the normal integrity of the trabecular meshwork. This is accomplished according to the present invention by the administration of angiostatic steroids.

It is believed that the angiostatic steroids disclosed herein function in the trabecular meshwork in a similar manner as shown by Ingber, et al., wherein it was shown that angiostatic steroids caused dissolution of the basement membrane scaffolding using a chick embryo neovascularization model; *Endocrinology*, 119, pp. 1768–1775 (1986). It is believed that the angiostatic steroids of the present invention prevent the accumulation, or promote the dissolution of, amorphous extracellular materials in the trabecular meshwork by inhibiting the formation of basement membrane materials and glycosaminoglycans. Thus, by preventing the development of these materials or promoting their dissolution, the normal integrity of the trabecular meshwork is retained and aqueous humor may flow through the trabecular meshwork at normal rates. As a result, the intraocular pressure of the eye is controlled.

The angiostatic steroids of the present invention may be incorporated in various formulations for delivery to the eye. For example, topical formulations can be used and can include ophthalmologically acceptable preservatives, surfactants, viscosity enhancers, buffers, sodium chloride and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin or white petrolatum. Sterile ophthalmic gel formulations comprising the angiostatic steroids of the present invention can be prepared by suspending an angiostatic steroid in a hydrophilic base prepared from a combination of, for example, Carbopol-940 (a carboxyvinyl polymer available from the B.F. Goodrich Company) according to published formulations for analogous ophthalmic preparations. Preservatives and tonicity agents may also be incorporated in such gel formulations.

The specific type of formulations selected will depend on various factors, such as the angiostatic steroid or its salt being used, and the dosage frequency. Topical ophthalmic aqueous solutions, suspensions, ointments and gels are the preferred dosage forms. The angiostatic steroid will normally be contained in these formulations in an amount of from about 0.005 to about 5.0 weight percent (wt. %). Preferable concentrations range from about 0.05 to about 2.0 wt. %. Thus, for topical administration, these formulations are delivered to the surface of the eye one to four times per day, depending upon the routine discretion of the skilled clinician.

In addition, antiinflammatory compositions of glucocorticoids can contain one or more angiostatic steroids of the present invention. These compositions will contain one or more glucocorticoids in an antiinflammatory effective amount and will contain one or more angiostatic steroids of the present invention in an amount effective to inhibit the IOP elevating effect of the glucocorticoids. The amount of each component will depend on various factors, such as the relative tendency of certain glucocorticoids to cause IOP elevations, the severity and type of ocular inflammation being treated, the estimated duration of the treatment, and so on. In general, the ratio of the amount of glucocorticoid to the amount of angiostatic steroid on a weight to weight basis will be in the range of 10:1 to 1:20. The concentration of the glucocorticoid component will typically be in the range of about 0.01% to about 2.0% by weight. The concentration of the angiostatic steroid component will typically be in the range of about 0.05% to about 5.0% by weight.

The following examples illustrate formulations and synthesis of compounds of the present invention, but are in no way limiting.

EXAMPLE 1

| Component | wt. % |
|---|---|
| Angiostatic Steroid | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 2

| Component | wt. % |
|---|---|
| 21-methyl-5β-pregnan-3α, 11β, 17α, 21-tetrol-20-one 21-methyl ether | 1.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

The 21α-methyl-5β-pregnan-3α, 11β, 17α, 21-tetrol-20-one 21 methyl ether is sterilized by either dry heat or ethylene oxide. If ethylene oxide sterilization is selected, aeration for at least 72 hours at 50° C. is necessary. The sterilized steroid is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 3

The following formulation is representative of the antiinflammatory compositions of the present invention.

| Component | wt. % |
|---|---|
| 4,9(11)pregnadien-17α,21-diol-3,20-dione-21-acetate | 1.0 |
| Dexamethasone | 0.1 |
| Tyloxapol | 0.01 to 0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared in the same manner set forth in Example 2, sterilizing and adding the dexamethasone to the steroid before placing both into a pressurized ballmill container.

EXAMPLE 4

Preparation of 5β-Pregnan-11β, 17α, 21-triol-20-one

Tetrahydrocortisol-F-21-t-butyldiphenylsilyl ether (PSO3842)

A solution of 4.75 g (17.3 mmol) of t-butyldiphenylchlorosilane in 5 mL of dry DMF was added dropwise to a stirred solution of 5.7 g (15.6 mmol) of tetrahydrocortisol-F (Steraloids No. P9050) and 2.3 g (19 mmol) of 4-dimethylaminopyridine (DNAP) in 30 mL of dry DHF, under $N_2$, at −25° to −30° C. (maintained with $CO_2$—MeCN). After a further 20 min at −30° C., the mixture was allowed to warm to 23° C. overnight.

The mixture was partitioned between ether and water, and the organic solution was washed with brine, dried ($MgSO_4$), filtered and concentrated to give 10.7 g of a white foam.

This material was purified by flash column chromatography (400 g silica; 62.5 to 70% ether/hexane). The 3-siloxy isomer eluted first, followed by mixed fractions, followed by the title compound. The concentrated mixed fractions (4.0 g) were chromatographed on the same column with 35% ethyl acetate/hexane. The total yield of the 3-siloxy isomer was 0.42 g (5%), and of the title compound, 5.05 g (53.5%). Continued elution with HeOH/EtOAc allowed recovery of unreacted tetrahydrocortisol-F.

PSO3842

NMR (200 HHz $^1$H) ($CDCl_3$): δ0.63 (s, 3H, me-18); 1.11 (s, 9H, t-Bu); 1.12 (s, 3H, me-19); 2.57 (t, J=13, 1H, H-8); 2.6 (s, 1H, OH-17); 3.63 (sept, J=2.5, 1H, H-3); 4.15 (br s, 1H, H-11); 4.37 and 4.75 (AB, J=20, 2H, H-21); 7.4 (m, 6H) and 7.7 (m, 4H) ($Ph_2$).

NHR (200 MHz $^1$H) (DMSO-$d_6$): δ0.64 (s, 3H, me-18); 1.02 (s, 9H, t-Bu); 1.07 (s, 3H, Me-19); 2.50 (t, J=13, 1H, H-8); 3.37 (m, 1H, H-3); 3.94 (d, J=2, 1H, OH-11); 4.00 (br s, 1H, H-11); 4.42 (d, J=5, 1H, OH-3); 4.38 and 4.83 (AB, J=20, 2H, H-21); 5.11 (s, 1H, OH-17); 7.45 (m, 6H) and 7.6 (m, 4H) ($Ph_2$).

NMR (50.3 - MHz $^{13}$C) ($CDCl_3$): 17.4 (C-18); 19.3 (C-16); 23.7 (C-15); 26.3 (C-7); 26.6 (C-19); ($Me_3$C); 27.2 (C-6); 30.9. (C-2); 31.5 (C-8); 34.1 ($Me_3$C); 34.8 (C-10); 35.2 (C-1); 36.2 (C-4); 39.7 (C-13); 43.5 (C-5); 44.3 (C-9); 47.4 (C-12); 52.1 (C-14); 67.8 (C-11); 68.9 (C-21); 71.7 (C-3); 89.8 (C-14); 127.8, 129.8, 132.8, 132.9, 135.7, 135.8 (diastereotopic $Ph_2$); 208.8 (C-20). Underlined resonances showed inversion in the APT experiment: Assignments: E. Breitmaler, W. Voelter "Carbon-13 NMR Spectroscopy," 3d ed., VCH, 1987; pp. 345–348.

IR (KBr) 3460, 2930, 2860, 1720, 1428, 1136, 1113, 1070, 1039, 703 cm$^{-1}$.

This compound dtd not show a sharp melting point but turned to a foam at 80°–100° C. Numerous attempts at recrystallization failed.

5β-Pregnan-11β17α, 21-triol-20-one

A solution of PS03842 (0.91 g, 1.50 mmol) and thiocarbonyl diimidazole (1.05 g, 5.9 mmol) in 8 mL of anhydrous dioxane was refluxed under $N_2$ for 3.5 h. The cooled solution was partitioned between ether and water and the organic solution was washed with brine, dried ($MgSO_4$), filtered and concentrated. The residue was chromatographed (120 g $SiO_2$, 35% EtOAc/hexane) giving 0.86 g (80%) of the imidazolyl thioester.

A solution of 0.75 g (1.05 mmol) of this compound in 100 mL of anhydrous dioxane was added dropwise over 2.2 h to a rapidly stirred, refluxing solution of 1.6 mL (5.9 mmol) of $Bu_3SnH$ in 100 mL of anhydrous dioxane under $N_2$. After & further 1 h at reflux, the solution was cooled, concentrated and the residue chromatographed (200 g $SiO_2$, 9% EtOAc/hexane) giving 0.43 g (70%) of the 3-deoxy-21-silyl ether. This material was dissolved in 20 mL of methanol; $Bu_4NF·3H_2O$ (0.50 g, 1.6 mmol) was added, and the mixture was heated to reflux under $N_2$ for 4 h. The cooled solution was diluted with 2 volumes of EtOAc, concentrated to ¼ volume, partitioned (EtOAc/$H_2O$), and the organic solution was washed with brine, dried ($MgSO_4$), filtered and concentrated. The residue (0.40 g) was chromatographed (30 g $SiO_2$, 40% EtOAc/hexane) to give 0.25 g (98%) of an oil. This oil was crystallized (n-BuCl) to afford 0.14 g of the title compound as a white solid, m.p. 167°–170° C.

IR (KBr): 3413 (br), 2934, 1714, 1455, 1389, 1095, 1035 cm$^{-1}$.

MS (CI): 351 (M+1).

NMR (200 MHz $^1$H, DMSO-$d_6$): δ0.69 (s, 3H, Me-18); 1.14 (s, 3H, Me-19); 0.8–2.0 (m); 2.5 (t, J=13, 1H, H-8); 3.96 (d, J=2, 1H, OH-11); 4.1 (br s, 1H, H-11); 4.1 and 4.5 (AB, further split by 5 Hz, 2H, H-21); 4.6 (t, J=5, 1H, OH-21); 5.14 (s, 1H, OH-17).

Anal. Calc'd for $C_{21}H_{34}O_4$: C, 71.96; H, 9.78. Found: C, 71.69; H, 9.66.

EXAMPLE 5

Preparation of 21-Methyl-5β-pregnan-3α, 11β, 17α, 21-tetrol-20-one 21-methyl ether Sodium hydride (60% oil dispersion, 0.10 g, 2.5 mmol) was added to a stirred solution of tetrahydrocortisol-F (0.73 g, 2.0 mmol) and $CH_3I$ (0.60 mL, 9.6 mmol) in 8 mL of anhydrous DMF under $N_2$. Hydrogen was evolved, and the temperature rose to 35° C. After 1 h, the mixture was diluted with EtOAc, extracted with water (until neutral) and brine, dried ($MgSO_4$), filtered and concentrated. The residue was chromatographed (70 g $SiO_2$, 80% EtOAc/hexane) to give 0.17 g of a white solid, RS (CI)=395 (M+1). This material was recrystallized (EtOAc-n-BuCl) to afford 0.12 g (16%) of the title compound as a feathery white solid, m.p. 208°–213° C.

IR (KBr): 3530, 3452, 2939, 2868, 1696 (s, CO), 1456, 1366, 1049 cm$^{-1}$.

NMR (200 MHz$^1$ H, DMSO-$d_6$): δ0.74 (s, 3H, Me-18); 1.09 (s, 3H, Me-19); 1.14 (d, J=6.6, 3H, C-21 Me); 0.8–2.0 (m); 2.47 (t, J=13, 1H, H-8); 3.18 (s, 3H, OMe); 3.35 (m, 1H, H-3); 4.00 (d, J=2, 1H, OH-11); 4.07 (br s, 1H, H-11); 4.37 (q, J=6.6, 1H, H-21); 4.43 (d, J=5, 1H, OH-3); 5.16 (s, 1H, OH-17).

Anal. Calc'd for $C_{23}H_{38}O_5$: C, 70.01; H, 9.71. Found: C, 70.06; H, 9.76.

EXAMPLE 6

Preparation of 3β-Azido-21-acetoxy-5β-pregnan-11β, 17α-diol-20-one

A solution of triphenylphosphine (2.6 g, 10 mmol) in 10 mL of toluene was carefully added to a stirred solution of PS03842 (see Example 4) (1.75 g, 2.90 mmol), diphenylphosphoryl azide (2.2 mL, 10.2 mmol) and diethyl azodicarboxylate (1.55 mL, 10 mmol) under $N_2$, keeping the internal temperature below 35° C. (exothermic). The solution was stirred for 1.2 h, then diluted with ether, washed with water and brine, dried ($MgSO_4$), filtered and concentrated and the residue (9.5 g, oil) chromatographed 175 g $SiO_2$, 15% EtOAc/hexane) giving 1.83 g of a viscous oil.

A solution of 1.73 g of this material and 1.75 g (5.5 mmol) of $Bu_4NF·3H_2O$ in 20 mL of methanol was refluxed under $N_2$ for 2.5 h. The crude product (1.94 g) was isolated with ethyl acetate and chromatographed (100 g $SiO_2$, 50% EtOAc/hexane) giving 0.60 g (56%) of a white semisolid. Trituration (4:1 hexane-ether) gave 0.57 g (53%) of a solid.

A stirred solution of 0.40 g of this material in 3 mL of dry pyridine was treated with 0.3 mL of acetic anhydride and stirred overnight at 23° C. under $N_2$. The mixture was quenched with 1 mL of methanol, stirred for 15 min, diluted with ether, washed with 1M aqueous HCl, water (until neutral), brine, dried (MgSO4), filtered and concentrated. The residue (0.41 g, oil) was chromatographed (35 g $SiO_2$, 33% EtOAc/hexane) to afford 0.33 g (76%) of the title compound as a white foam, m.p. 80°–90° C. (dec).

IR (KBr): 3505, 2927, 2866, 2103 (vs), 1721 (sh 1730), 1268, 1235 $cm^{-1}$.

NMR (200 MHz $^1$H, $CDCl_3$): δ0.92 (s, 3H, Me-18); 1.21 (s, 3H, Me-19); 1.0–2.1 (m); 2.17 (s, 3H, Ac); 2.25 (s 1H, OH-17); 2.74 (m, 1H, H-8); 3.97 (br s, 1H, H-3); 4.31 (br s, 1H, H-11); 4.94 (AB, J-17, Δv=60, 2H, H-21).

Anal. Calc'd for $C_{23}H_{35}N_3O_5$: C, 63.72; H, 8.14; N, 9.69. Found: C, 63.39; H, 8.18; N, 9.45.

EXAMPLE 7

Preparation of 3β-Acetamido-21-acetoxy-5β-pregnan-11β, 17α-diol -20-one

A solution of 3β-azido-21-acetoxy-5β-pregnan-11β,17α-diol-20-one (0.15 g, 0.35 mmol) in 8 mL of absolute ethanol containing 0.03 g of 10% Pd on C was stirred under $H_2$ (1 atm) at 23° C. for 2 h. The mixture was filtered and concentrated, the residue dissolved in EtOAc, the bastc material extracted into 1M aqueous HCl, liberated ($Na_2CO_3$), extracted (EtOAc) and the organic extract washed with water (until neutral) and brine, dried ($NgSO_4$), filtered and concentrated to provide 58 mg of a solid.

This material was acetylated (1.0 mL of dry pyridine, 0.20 mL of $Ac_2O$, 23° C., $N_2$, overnight), followed by workup (as described for the steroid of Example 6 [last step]) affording a crude product that was chromatographed (25 g $SiO_2$;, EtOAc). This product was triturated with ether to afford 51 mg (33%) of product as a white solid, m.p. 179°–181° C.

Ms (CI, tsobutane): (M+1)=450 ($M^+$), 432, 391, 371, 348. IR (KBr): 3398 (br), 2932, 2865, 1720 (sh. 1740), 1652, 1538, 1375, 1265, 1236 $cm^{-1}$.

NHR (200 MHz $^1$H, $CDCl_3$): 60.89, 1.22, 1.99, 2.17 (all s, 3H); 1.0–2.2 (m); 2.7 (t, J=13, 1H, H-8);. 3.03 (s, 1H, OH-17); 4.2 (br s, 1H, H-11); 4.3 (br s, 1H, H-3); 4.96 (AB, J=17.5, Δv=42, 2H, H-21); 5.8 (d, J=10, 1H, NH).

We claim:

1. A method for controlling ocular hypertension associated with primary open angle glaucoma which comprises administering a pharmaceutically effective amount of a compound selected from the group consisting of 21-methyl-5β-pregnan-3α11β, 17α, 21-tetrol-20-one 21-methyl ether; 3β-azido-21-acetoxy-5β-pregnan-11β, 17α-diol-20-one; 3β-acetamido-21-acetoxy-5β-pregnan-11β, 17α-diol-20-one; 5β-pregnan-11β, 17α,21-triol-20-one; and 4,9(11)-pregnadien-17α,21-diol-3,20-dione-21 -acetate.

2. A composition for controlling ocular hypertension comprising a pharmaceutically effective amount of a compound selected from the group consisting of: 21-methyl-5β-pregnan-3α,11β,17α, 21-tetrol-20-one 21-methyl ether; 3β-azido-21-acetoxy-5β-pregnan-11β, 17α-diol-20-one; 3β-acetamido-21-acetoxy-5β-pregnan-11β, 17α-diol-20-one; 5β-pregnan-11β, 17α, 21-triol-20-one; and 4, 9(11)-pregnadien-17α,21-diol-3,20-dione-21-acetate.

3. The composition of claim 2 wherein the compound is present at a concentration between 0.005 and 5.0 weight percent.

* * * * *